United States Patent [19]

Habicht et al.

[11] 4,017,629
[45] Apr. 12, 1977

[54] CERTAIN 1,4-DIHYDRO-3-SULFINYL OR SULFONYL-PYRIDINES

[75] Inventors: Ernst Habicht, Oberwil; Hans Kühnis, Basel, both of Switzerland

[73] Assignee: Ciba-Geigy Corporation, Ardsley, N.Y.

[22] Filed: May 28, 1975

[21] Appl. No.: 581,523

[30] Foreign Application Priority Data

June 4, 1974 Switzerland ............ 7638/74

[52] U.S. Cl. .................. 424/266; 260/247.1 H; 260/247.1 M; 260/247.2 A; 260/268 H; 260/293.69; 260/294.8 F; 260/294.9; 260/295.5 R; 424/267
[51] Int. Cl.[2] ............ A61K 31/455; C07D 211/86
[58] Field of Search ............ 260/294.8 F, 293.69; 424/266, 267

[56] References Cited

UNITED STATES PATENTS 3,867,393  2/1975  Meyer et al. ............ 260/294.8 F
3,883,540  5/1975  Meyer et al. ............ 260/294.9

Primary Examiner—Alan L. Rotman
Attorney, Agent, or Firm—Joseph G. Kolodny; John J. Maitner; Theodore O. Groeger

[57] ABSTRACT

The present invention relates to 1,4-dihydropyridines of the formula I

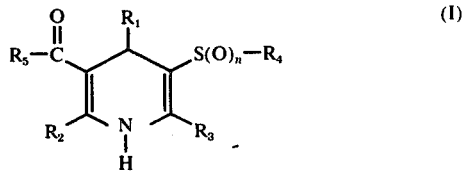

and their tautomers, wherein $R_1$ represents an aryl radical, $R_2$ and $R_3$ independently of one another represents hydrogen or a hydrocarbon radical, $R_4$ represents an alkyl, aryl or aralkyl radical, $R_5$ denotes an alkoxy radical, which is optionally substituted by an amino group, or denotes an amino group and $n$ is 1 or 2, especially to the 2,6-dimethyl-3-carbomethoxy-5-methylsulphonyl-4-(2-trifluoromethylphenyl)-1,4-dihydropyridine and to the 2,6-dimethyl-3-carbomethoxy-5-methylsulphonyl-4-(2-nitrophenyl)-1,4-dihydropyridine.

They have an antihypertensive activity.

15 Claims, No Drawings

CERTAIN 1,4-DIHYDRO-3-SULFINYL OR SULFONYL-PYRIDINES

The invention relates to new 1,4-dihydropyridines of the formula I

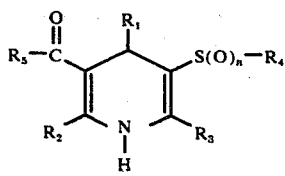

and their tautomers, wherein $R_1$ represents an aryl radical, $R_2$ and $R_3$ independently of one another represent hydrogen or a hydrocarbon radical, $R_4$ represents an alkyl, aryl or aralkyl radical, $R_5$ denotes an alkoxy radical, which is optionally substituted by an amino group, or denotes an amino group and $n$ is 1 or 2, as well as processes for their manufacture.

An aryl radical $R_1$ is, for example, an unsubstituted, or especially a substituted phenyl radical. A substituted phenyl radical can carry 1, 2 or 3 identical or different substitutents. Examples of possible substituents are lower alkyl radicals, hydroxyl groups, lower alkoxy groups, halogen atoms, lower alkenyl groups, lower alkenyloxy groups, amino groups, which are optionally monosubstituted or disubstituted by lower alkyl radicals, or preferably lower alkanoyl radicals, carbamyl groups which are optionally monosubstituted or disubstituted by lower alkyl radicals or disubstituted by lower alkylene, oxaalkylene, thiaalkylene or azaalkylene radicals, or lower alkoxycarbonyl groups, carboxyl groups, lower alkanoyloxy groups or, above all, nitro groups, trifluoromethyl groups, cyano groups, azido groups, or sulphamyl groups, which are optionally monosubstituted or disubstituted by lower alkyl radicals or disubstituted by lower alkylene, oxaalkylene, thiaalkylene or azaalkylene radicals. The substituents mentioned are preferably in the ortho-position but can also occupy the meta-position or para-position.

A hydrocarbon radical $R_2$ and/or $R_3$ is preferably a phenyl radical, a phenyl-lower alkyl radical or especially a lower alkyl radical.

$R_4$ is especially a lower alkyl radical, or also a phenyl radical or phenyl-lower alkyl radical, which is optionally polysubstituted, or especially monosubstituted, by lower alkyl, lower alkoxy, halogen and/or trifluoromethyl.

An amino group $R_5$, or amino in an aminoalkoxy group $R_5$, is an unsubstituted amino group or especially an amino groups which is monosubstituted or disubstituted by lower alkyl radicals or monosubstituted by cycloalkyl or disubstituted by a lower alkylene, oxaalkylene, thiaalkylene or azaalkylene radical.

Unless otherwise indicated, lower radicals in the preceding and following text are to be understood as those radicals which contain at most 7, above all at most 4, carbon atoms.

A phenyl-lower alkyl radical is, above all, a 3-phenylpropyl or 2-phenylpropyl radical or especially a phenylethyl or benzyl radical.

An alkoxy group is especially a lower alkoxy group. A lower alkoxy group is especially a methoxy or ethoxy group or a straight-chain or branched propoxy, butoxy, pentyloxy or hexyloxy group.

An aminoalkoxy group is especially an amino-lower alkoxy group, such as an aminoethoxy or aminopropoxy group. The amino group therein is unsubstituted or, above all, monosubstituted or disubstituted by lower alkyl radicals, such as methyl or ethyl radicals, or disubstituted by a lower alkylene or oxaalkylene radical.

A lower alkyl radical is especially a methyl, ethyl, n-propyl or isopropyl radical or a straight-chain or branched butyl, pentyl, hexyl or heptyl radical, which is bonded in any desired position.

A cycloalkyl radical is especially a cycloalkyl radical with 3–8, especially 3–5, carbon atoms in the ring, such as, for example, the cyclopropyl, cyclobutyl or cyclopentyl radical.

Lower alkylene radicals are especially straight-chain or branched lower alkylene radicals with 3–7, especially 4–6, carbon atoms in the alkylene chain, such as, for example, but-1,4-ylene, pent-1,5-ylene or hex-1,6-ylene or hept-2,6-ylene radicals.

An oxa-lower alkylene radical is, for example, a branched, or especially a straight-chain, oxa-lower alkylene radical with, in particular, 4 or 5 carbon atoms in the oxalower alkylene chain and, above all, is the 3-oxa-pent-1,5-ylene radical.

A thia-lower alkylene radical is, for example, a branched, or especially a straight-chain, thia-lower alkylene radical with, in particular, 4 or 5 carbon atoms in the thialower alkylene chain and, above all, is the 2-thia-pent-1,5-ylene radical.

An aza-lower alkylene radical is, for example, a branched, or especially a straight-chain, aza-lower alkylene radical with 4-6 carbon atoms in the aza-lower alkylene chain, in which the nitrogen atom can be substituted by a lower alkyl radical, such as especially the methyl or ethyl radical, or the 2-hydroxyethyl radical, and, above all, is a 3-aza-pent-1,5-ylene radical, in which the nitrogen atom can be substituted as indicated.

Halogen atoms are especially those with an atomic number of at most 35, for example, fluorine or bromine or especially chlorine.

Lower alkenyl radicals are, for example, methallyl or especially allyl radicals.

Lower alkenyloxy radicals are, for example, methallyloxy radicals or especially allyloxy radicals.

Lower alkanoyl radicals are, above all, butyryl, propionyl or acetyl radicals.

Lower alkanoyloxy radicals are, above all, butyryloxy, propionyloxy or acetoxy radicals.

Lower alkoxycarbonyl radicals are especially those which contain the lower alkoxy radicals mentioned and are above all ethoxycarbonyl or methoxycarbonyl radicals.

The new compounds possess valuable pharmacological properties, above all an action on the blood pressure. Thus, for example, they possess an anti-hypertensive action, as can be demonstrated, for example, on renal-hypertonic dogs at doses of 1 to 30 ml/kg administered perorally, or on renalhypertonic rats at doses of 3 to 300 mg/kg administered perorally. The new compounds also possess a vasodilating action, as can be demonstrated, for example, by the determination of the peripheral total resistance on narcotised dogs with doses of, for example, 10 mg/kg administered intraduodenally. Furthermore, the new compounds possess a dilating action on the coronary vessels, as can be demonstrated, for example, in vitro on isolated guinea pig hearts by the Langendorff method at doses of 0.1 to 10 μg/kg. The new compounds possess a low toxicity.

The new compounds can therefore be used as antihypertensive agents, vasodilators and as coronary dilators. However, the new compounds are also valuable intermediates for the manufacture of other useful substances, especially pharmaceutically active compounds.

The invention relates above all to 1,4-dihydropyridines of the formula I, wherein $R_1$ is unsubstituted phenyl or especially phenyl substituted by the above-mentioned substituents, $R_2$ and $R_3$ independently of one another represent hydrogen, phenyl, phenyl-($C_{1-4}$)-alkyl or ($C_{1-7}$)-alkyl, $R_4$ represents ($C_{1-7}$)-alkyl or unsubstituted phenyl or phenyl substituted by ($C_{1-4}$)-alkyl, ($C_{1-4}$)-alkoxy, halogen and/or trifluoromethyl, and $R_5$ represents ($C_{1-4}$)-lower alkoxy, amino, mono- or di-($C_{1-4}$)-alkylamino, alkyleneamino with 4–6 carbon atoms, oxaalkyleneamino with 3–5 carbon atoms in the ring, thiaalkyleneamino with 3–5 carbon atoms in the ring, aza-lower alkyleneamino with 3–5 carbon atoms in the ring, $N'$-($C_{1-4}$)-lower alkylaza-lower alkyleneamino with 3–5 carbon atoms in the ring, amino-lower alkoxy, mono- or di-($C_{1-4}$)-alkylamino-lower alkoxy, ($C_{4-6}$)-alkyleneamino-lower alkoxy or ($C_{3-5}$)-oxaalkyleneamino-lower alkoxy.

The invention also relates above all to 1,4-dihydropyridines of the formula I, wherein $R_1$ represents a phenyl radical which is substituted by 1 to 3 identical or different substituents from the group nitro, trifluoromethyl, cyano, azido, lower alkanoyl, sulphamoyl, N-($C_{1-4}$)-alkylsulphamoyl, N,N-di-($C_{1-4}$)-alkylsulphamoyl, alkyleneaminosulphonyl with 4–6 carbon atoms in the ring, oxa-lower alkyleneaminosulphonyl with 4–5 carbon atoms in the ring, thia-lower alkyleneaminosulphonyl with 4–5 carbon atoms in the ring, aza-lower alkyleneaminosulphonyl with 4–5 carbon atoms in the ring or ($C_{1-4}$)-lower alkoxycarbonyl, at least one of the substituents being in the ortho-position, $R_2$ and $R_3$ independently of one another represent hydrogen, phenyl or ($C_{1-4}$)-alkyl, $R_4$ represents ($C_{1-7}$)-alkyl, phenyl, ($C_{1-4}$)-alkylphenyl, ($C_{1-4}$)-alkoxyphenyl, halogenophenyl or trifluoromethylphenyl, $R_5$ represents amino, mono- or di-($C_{1-4}$)-alkylamino, ($C_{4-6}$)-alkyleneamino or especially ($C_{1-4}$)-alkoxy, amino-($C_{1-4}$)-alkoxy, mono- or di-($C_{1-4}$)-alkylamino-($C_{1-4}$)-alkoxy or ($C_{4-6}$)-alkyleneamino-($C_{1-4}$)-alkoxy and n is 1 or 2.

The invention also relates above all to 1,4-dihydropyridines of the formula I, wherein $R_1$ represents a phenyl radical which is substituted by 1 or 2 identical or different substituents from the group nitro, trifluoromethyl, cyano, azido, ($C_{1-4}$)-lower alkanoyl, sulphamoyl, N-($C_{1-4}$)-alkylsulphamoyl and N,N-($C_{1-4}$)-dialkylsulphamoyl, at least one of the substituents being in the ortho-position, $R_2$ and $R_3$ independently of one another represent hydrogen, ($C_{1-4}$)-alkyl or phenyl, $R_4$ represents ($C_{1-4}$)-alkyl or phenyl, $R_5$ represents amino, mono- or di-($C_{1-4}$)-alkylamino, ($C_{4-6}$)-alkyleneamino or especially ($C_{1-4}$)-alkoxy or di-($C_{1-4}$)-alkylamino-($C_{1-4}$)-alkoxy and $n$ is 1 or preferably 2.

The invention also relates above all to 1,4-dihydropyridines of the formula I, wherein $R_1$ denotes a phenyl radical which is substituted in the ortho-position by cyano, azido, ($C_{1-4}$)-lower alkanoyl, sulphamoyl, N-($C_{1-3}$)-alkylsulphamoyl or especially by nitro, trifluoromethyl or N,N-di-($C_{1-3}$)-alkylsulphamoyl, $R_2$ and $R_3$ independently of one another represent hydrogen, ($C_{1-4}$)-alkyl or phenyl, $R_4$ represents ($C_{1-4}$)-alkyl or phenyl, $R_5$ represents amino, ($C_{1-4}$)-lower alkylamino, ($C_{1-4}$)-di-lower alkylamino or especially ($C_{1-4}$)-alkoxy, ($C_{4-6}$)-alkyleneamino or di-($C_{1-4}$)-lower alkylamino-($C_{1-4}$)-alkoxy and n is 1 or preferably 2.

The invention also relates above all to 1,4-dihydropyridines of the formula I, wherein $R_1$ denotes a phenyl radical which is substituted in the ortho-position by cyano, acetyl or sulphamoyl or especially by nitro, trifluoromethyl or N,N-di-($C_{1-3}$)-alkylsulphamoyl, $R_2$ and $R_3$ independently of one another denote hydrogen, methyl, ethyl or phenyl, $R_4$ represents methyl, ethyl or phenyl, $R_5$ represents amino, methylamino, dimethylamino or especially methoxy, ethoxy, piperidino, dimethylaminoethoxy or diethylaminoethoxy and n is 1 or preferably 2.

Thus, for example, 2,6-dimethyl-3-carbomethoxy-5-methylsulphonyl-4-(2-trifluoromethylphenyl)-1,4-dihydropyridine or 2,6-dimethyl-3-carbomethoxy-5-methylsulphonyl-4-(2-nitrophenyl)-1,4-dihydropyridine shows a distinct antihypertensive action on renal-hypertonic dogs at a dose of 1 mg/kg administered perorally.

The new compounds can be obtained according to methods which are in themselves known.

Thus, for example, the procedure followed can be such that a compound of the formula II is reacted with a compound of the formula III

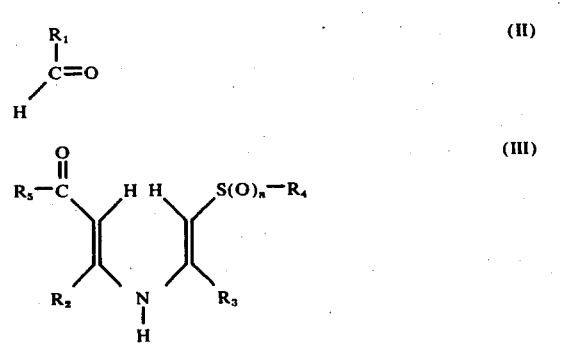

wherein $R_1$, $R_2$, $R_3$, $R_4$, $R_5$ and $n$ have the above meanings.

The reaction is carried out in the customary manner, for example by first introducing the compound of the formula II in a dipolar aprotic solvent, such as, for example, dimethylformamide, dimethylsulphoxide, acetonitrile or hexamethylphosphoric acid triamide, and thereafter adding the compound of the formula III. However, it is also possible to vary the sequence of the reactants. The reaction is carried out at room temperature or preferably at elevated temperature, such as, for example, at 200° C, and, if necessary, in a closed vessel and/or in an inert gas atmosphere, for example a nitrogen atmosphere.

However, the reaction can also be carried out by reacting a compound of the formula II with a compound of the formula IV and with a compound of the formula V

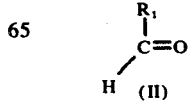

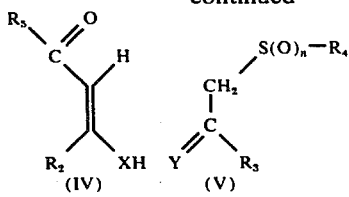

wherein $R_1$, $R_2$, $R_4$, $R_5$ and $n$ have the above meanings and one of the symbols X and Y represents O and the other represents NH. The compounds of the formulae IV and V can also be employed in the form of their tautomers.

The reaction is carried out in the customary manner and preferably by first introducing the compound of the formula II in a dipolar, aprotic solvent, such as, for example, dimethylformamide, dimethylsulphoxide, acetonitrile or, surprisingly, especially in hexamethylphosphoric acid triamide, and thereafter adding the compounds of the formulae IV and V. However, it is also possible to vary the sequence of the reactants. The compound of the formula V is preferably added in about 10 to 50% excess but can also be employed in an equimolar amount. The reaction is carried out at room temperature or preferably at elevated temperature, such as, for example, at 220° C, and, if necessary, in a closed vessel and/or in an inert gas atmosphere, for example a nitrogen atmosphere.

However, the reaction can further also be carried out by reacting a compound of the formula II with a compound of the formula VI, with a compound of the formula VII and with ammonia

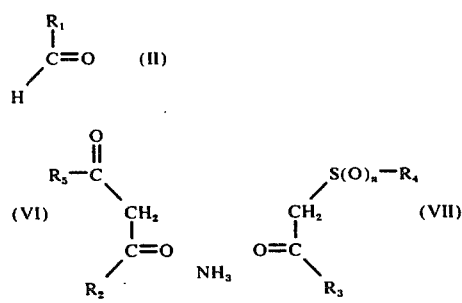

wherein $R_1$, $R_2$, $R_3$, $R_4$, $R_5$ and $n$ have the abovementioned meanings.

The reaction is carried out in the customary manner and preferably in such a way that the reactants II, VI and VII are added in equimolar amounts and the ammonia is added in excess. The reactants can be added in any desired sequence but preferably the compounds VI and VII are added to compound II and the ammonia is then allowed to act on the mixture. Suitable solvents, in addition to water, are all inert organic solvents, such as lower alkanols, for example methanol, ethanol, isopropanol and tert.-butyl alcohol, open chain or cyclic ethers, for example diethyl ether, tetrahydrofurane or dioxane, glacial acetic acid, acetonitrile or hexamethylphosphoric acid triamide. The reaction can be carried out at room temperature or at elevated temperature, for example at 200° C, and especially at the boiling point of the solvent and, if necessary, in a closed vessel and/or in an inert gas atmosphere, for example a nitrogen atmosphere. The ammonia can be added in the liquid form or in the form of a solution, but preferably in the gaseous form.

In the abovementioned reactions, the aldehyde of the formula II can also be employed in the form of its reactive functional derivatives, such as, for example, in the form of its hydrates, acetals, oximes, hydrazones, semicarbazones or bisulphite addition products.

Furthermore, the new compounds can also be manufactured by reacting a compound of the formula VIII

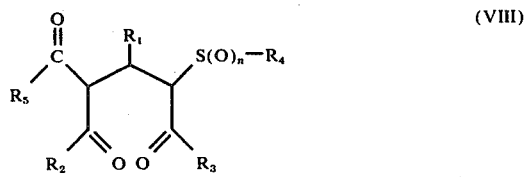

wherein $R_1$, $R_2$, $R_3$, $R_4$, $R_5$ and $n$ have the abovementioned meanings, with ammonia.

The reaction is carried out in the customary manner and preferably in such a way that the ammonia is added in excess. Suitable solvents, in addition to water, are all inert organic solvents, such as lower alkanols, for example methanol, ethanol, isopropanol or tert.-butyl alcohol, open chain or cyclic ethers, for example diethyl ether, tetrahydrofurane or dioxane, glacial acetic acid, pyridine, dimethylformamide, dimethylsulphoxide, acetonitrile or hexamethylphosphoric acid triamide. The reaction can be carried out at room temperature or at elevated temperature, for example at 200° C, and especially at the boiling point of the solvent, and, if necessary, in a closed vessel and/or in an inert gas atmosphere, for example a nitrogen atmosphere. The ammonia can be added in the liquid form or the form of a solution, but preferably in the gaseous form.

Furthermore, the new compounds can also be obtained by reacting a compound of the formula IX

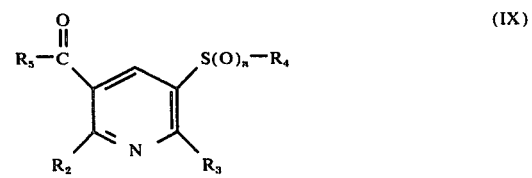

wherein $R_2$, $R_3$, $R_4$, $R_5$ and $n$ have the abovementioned meanings, with a compound of the formula X $$R_1 - Z \qquad\qquad X.$$

wherein $R_1$ has the abovementioned meanings and Z represents a metal atom. A metal atom is, in particular, an alkaline earth metal atom, a metal atom from the zinc group, or, above all, an alkali metal atom. An alkaline earth metal atom or a metal atom from the zinc group is, for example, a zinc, cadmium or magnesium atom, these being bonded, by means of the free valency, to a second radical $R_1$ or preferably to a halogen atom, such as chlorine, iodine, or, above all, bromine. An alkali metal atom is, for example, a sodium, potassium or, above all, a lithium atom. Thus, a metal atom Z is preferably to be understood as a group of the formula —Zn-Hal or, above all, —Cd-Hal or —Mg-Hal, wherein Hal represents chlorine, iodine or, above all, bromine, or a group of the formula $-Zn_{1/2}$, $-Cd_{1/2}$ or —Mg$_{1/2}$ or a sodium, potassium or, above all, a lithium atom.

The reaction is carried out in the customary manner. Preferably an inert solvent is used for the reaction, such as a lower aliphatic ether, for example dibutyl ether or, above all, diethyl ether or diisopropyl ether, or a cyclic ether, for example dioxane or, above all, tetrahydrofurane, or, for example in the reaction with cadmium compounds, a hydrocarbon, preferably an aromatic hydrocarbon, such as benzene, or, for example in the reaction with lithium compounds, a mixture of an ether and a hydrocarbon, preferably an aliphatic hydrocarbon, above all an alkane, such as tetrahydrofurane/hexane. The reaction is preferably carried out at a lowered temperature, for example between −70° C and room temperature, or at moderately elevated temperature, for example up to 100° C, and, if necessary, in a closed vessel and/or in an inert gas atmosphere, for example a nitrogen atmosphere.

In resulting compounds of the formula I, substituents can be introduced, modified or split off in the customary manner within the scope of the end products.

The invention also relates to those embodiments of the process in accordance with which a compound obtainable as an intermediate product at any stage of the process is used as a starting material and the missing process steps are carried out, or the process is discontinued at any stage, or in which a starting material is formed under the reaction conditions, or in which a reactant is present, if appropriate, in the form of its derivatives, such as its salts, and/or addition compounds and/or its racemate, a mixture of its diastereomers or in the form of its antipodes.

Appropriately, those starting materials which lead to the groups of end products mentioned particularly in the preceding text, and especially to the end products described or mentioned specifically, are used for carrying out the reactions according to the invention.

The starting materials are known or, if they are new, can be obtained in accordance with methods which are in themselves known.

Compounds of the formula III can be obtained, for example, by reacting a compound of the formula XI with a compound of the formula XII and with ammonia

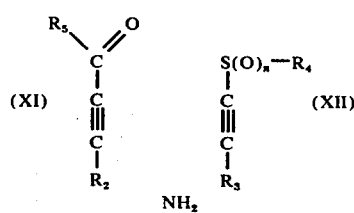

wherein $R_2$, $R_3$, $R_4$, $R_5$ and $n$ have the above meanings.

Compounds of the formula IV, wherein X represents NH, can be obtained, for example, by reacting a compound of the formula IV, wherein X represents O, with ammonia.

Compounds of the formula V, wherein Y represents an oxygen atom, can be manufactured, for example, by reacting a compound of the formula XIII

wherein $R_3$ has the above meanings and A represents a nucleophilic group which can be split off, for example a lower alkoxy group, such as the methoxy group, or a halogen atom, such as a chlorine, bromine or iodine atom, or an azido group, with a compound of the formula XIV

wherein $M^+$ preferably represents an alkali metal cation and $R_4$ and $n$ have the above meanings.

Starting materials of the formula VI can be obtained, for example, by reacting a compound of the formula XV

wherein $R_5$ has the above meanings, with a compound of the formula XVI

wherein $R_2$ and A have the above meanings, under strongly basic conditions, for example in the presence of a lower alkanolate, such as a methanolate or ethanolate.

Compounds of the formula VIII can be obtained, for example, by reacting a compound of the formula VI with a compound of the formula XVIII

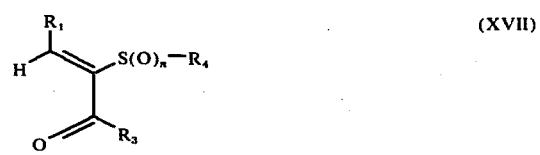

wherein $R_1$, $R_3$, $R_4$ and $n$ have the above meanings, under strongly basic conditions, for example in the presence of a lower alkanolate, such as a methanolate or ethanolate.

The reactions mentioned for the manufacture of the compounds of the formula I or of the starting materials can optionally be carried out simultaneously or consecutively and in any desired sequence.

The reactions mentioned are carried out in the customary manner in the presence or absence of diluents, condensation agents and/or catalytic agents, at lowered, normal or elevated temperature and, if appropriate, in a closed vessel.

Depending on the starting materials and methods selected, the new compounds can be present as optical antipodes or racemates or, in so far as they contain at least two asymmetric carbon atoms, also as mixtures of isomers (mixtures of diastereoisomers).

Resulting mixtures of isomers (mixtures of diastereoisomers) can be separated, by virtue of the physicochemical differences of the constituents, into the two stereoisomeric (diastereomeric) pure racemates in a known manner, for example by chromatography and/or fractional crystallisation.

Resulting racemates can be separated by known methods, for example by recrystallisation from an optically active solvent or with the aid of micro-organisms.

The new compounds can be used as medicaments, for example in the form of pharmaceutical preparations, in which they are present in a mixture with a pharmaceutical, organic or inorganic, solid or liquid excipient, which is suitable, for example, for enteral, for example oral, or parenteral administration. Possible substances for making up the latter are those which do not react with the new compounds, such as, for example, water, gelatine, lactose, starch, magnesium stearate, talc, vegetable oils, benzyl alcohols, gum, polyalkylene glycols, white petroleum jelly, cholesterol or other known medicinal excipients. The pharmaceutical preparations can be, for example, tablets, dragees, capsules or suppositories, or in liquid form as solutions (for example as an elixir or syrup), suspensions or emulsions. If appropriate, they are sterilised and/or contain auxiliaries, such as preservatives, stabilisers, wetting agents or emulsifiers, salts for modifying the osmotic pressure or buffers. They can also contain yet further therapeutically valuable substances. The preparations, which can also be used in veterinary medicine, are obtained according to customary methods.

The daily dose is about 3–1,500 mg, administered perorally, in the case of a mammal having a body weight of about 75 kg and is preferably administered in single doses of 3–100 mg.

The examples which follow illustrate the invention without, however, restricting it.

EXAMPLE 1

8.0 g of aminocrotonic acid methyl ester and 13.6 g of methylsulphonylacetone are aded to 12.2 g of o-trifluoromethyl-benzaldehyde dissolved in 75 ml of hexamethylphosphoric acid triamide. The mixture is then stirred for 6 hours at a bath temperature of 100° to 110° C. The mixture is cooled and extracted by shaking with a solution of 450 ml of water, 450 ml of ethyl acetate, 75 ml of methanol and 75 ml of saturated sodium chloride solution.

The organic phase is separated off and washed with 3 times 150 ml of water, with twice 75 ml of saturated sodium carbonate solution and once with 75 ml of 2 N sodium carbonate solution. The yellowish ethyl acetate solution is dried with sodium sulphate and evaporated. Fractional crystallisation of the residue from methylene chloride/ether gives 2,6-dimethyl-3-carbomethoxy-5-methylsulphonyl-4-(2-trifluoromethylphenyl)-1,4-dihydropyridine of melting point 160°–163° C.

EXAMPLE 2

23.0 g of aminocrotonic acid methyl ester and 40.8 g of methylsulphonylacetone are added to 30.2 g of o-nitrobenzaldehyde dissolved in 200 ml of hexamethylphosphoric acid triamide. The mixture is then stirred for 3 hours at a bath temperature of 90°–100° C. The mixture is cooled and dissolved in 1,000 ml of ethyl acetate and the solution is washed with 400 ml of half-saturated sodium chloride solution, with twice 200 ml of 2 N sodium carbonate solution and with twice 500 ml of water. The ethyl acetate solution is dried with sodium carbonate and evaporated. Crystallisation of the residue from ethyl acetate/ether gives 2,6-dimethyl-3-carbomethoxy-5-methylsulphonyl-4-(2-nitrophenyl)-1,4-dihydropyridine of melting point 211°–212° C.

EXAMPLE 3

6.4 g of o-dimethylaminosulphamyl-benzaldehyde, 3.5 g of 3-aminocrotonic acid methyl ester and 5.4 g of methylsulphonylacetone are stirred in 30 ml of hexamethylphosphoric acid triamide for 6 hours under nitrogen at a bath temperature of 110° C. The mixture is cooled and dissolved in 200 ml of ethyl acetate and the solution is washed with a mixture of 200 ml of water, 30 ml of methanol and 30 ml of sodium chloride solution. The aqueous phase is separated off and the organic phase is washed with three times 50 ml of water, with twice 30 ml of saturated sodium bicarbonate solution and once with 30 ml of 2 N sodium carbonate solution. The yellowish solution is dried over sodium sulphate and evaporated and the residue is taken up in chloroform. A small amount of insoluble matter is filtered off, the filtrate is evaporated and the residual oil is recrystallised from methylene chloride/ether. 2,6-Dimethyl-5-carbomethoxy-5methylsulphonyl-4-(2-dimethylaminosulphamyl-phenyl)-1,4-dihydropyridine, which is thus obtained, melts at 218°–221° C.

EXAMPLE 4

10.9 g of o-nitrobenzaldehyde, 10.3 g of 3-aminocrotonic acid dimethylaminoethyl ester and 8.2 g of methylsulphonylacetone are stirred in 50 ml of hexamethylphosphoric acid triamide for 8 hours under nitrogen at a bath temperature of 110° C. The mixture is cooled and dissolved in 400 ml of ethyl acetate and the solution is washed with a mixture of 400 ml of water, 60 ml of methanol and 60 ml of sodium chloride solution. The aqueous phase is separated off and the organic phase is treated three times with 100 ml of water and twice with 100 ml of 1 N hydrochloric acid. The acid phase is rendered alkaline with concentrated ammonia, extracted with ethyl acetate, dried and evaporated. The residue is chromatographed on silica gel in a mixture of chloroform (9):methanol (1). The product is twice treated in methanol with animal charcoal, the filtrate is evaporated to dryness and moisture still adhering is removed with benzene. 2,6-Dimethyl-3-(2-dimethylamino)-carboethoxy-4-(2-nitrophenyl)-5methylsulphonyl-1,4-dihydropyridine which is thus obtained, is recrystallised from ether and has a melting point of 79°–83° C.

EXAMPLE 5

4.5 g of o-nitrobenzaldehyde, 6.3 g of 3-aminocrotonic acid tert.-butyl ester and 4.1 g of methylsulphonylacetone are stirred in 30 ml of hexamethylphosphoric acid triamide for 8 hours under nitrogen at a bath temperature of 110° C. The mixture is cooled and dissolved in 200 ml of ethyl acetate and the solution is treated with a mixture of 200 ml of water, 30 ml of methanol and 30 ml of sodium chloride solution. The aqueous phase is separated off and the organic phase is washed three times with 50 ml of water, twice with 50 ml of 1 N hydrochloric acid, twice with 50 ml of sodium bicarbonate and once with 50 ml of 2 N sodium carbonate solution. The organic phase is separated off and dried. The residue is recrystallised from isopropanol. 2,6-Dimethyl-3-carbotert.-butoxy-4-(2-nitrophenyl)-5-methylsulphonyl-1,4-dihydro pyridine, which is thus obtained, melts at 152°–155° C.

EXAMPLE 6

15.1 g of o-nitrobenzaldehyde, 16.8 g of 3-aminocrotonic acid piperidide and 13.6 g of methylsulphonylacetone are stirred in 100 ml of hexamethylphosphoric acid triamide for 10 hours under nitrogen at a bath temperature of 115° C. The mixture is cooled and dissolved in 600 ml of ethyl acetate and the solution is washed with a mixture of 600 ml of water, 90 ml of methanol and 90 ml of sodium chloride solution. The organic phase is separated off and the aqueous phase, in which a dark brown product precipitates, is filtered. The crystalline product is dried by azeotropic distillation on a rotary evaporator and treated twice in methanol/chloroform with animal charcoal. The filtrate is evaporated and the residue is recrystallised from isopropanol. 2,6-Dimethyl-3-piperidinocarbonyl-4-(2-nitrophenyl)-5-methylsulphonyl-1,4-dihydropyridine, which is thus obtained, melts at 275°–276° C.

EXAMPLE 7

9.2 g of 3-aminocrotonic acid methyl ester and 20 g of methylsulphonylacetophenone are added to 12 g of o-nitro-benzaldehyde benzaldehyde dissolved in 70 ml of hexamethylphosphoric acid triamide. The mixture is then stirred for 10 hours under nitrogen at a bath temperature of 110°C. The mixture is cooled and dissolved in 600 ml of ethyl acetate and the solution is washed with a mixture of 600 ml of water, 90 ml of methanol and 90 ml of saturated sodium chloride solution. The aqueous phase is separated off and the organic phase is shaken with 3 times 150 ml of water, with twice 90 ml of saturated sodium bicarbonate solution, with twice 150 ml of 1 N hydrochloric acid solution and once with 90 ml of 2 N sodium carbonate solution. The ethyl acetate phase is dried over sodium sulphate and evaporated. Crystallisation of the residue from ethyl alcohol gives a yellow crystalline product, which is freed from the methyl-sulphonylacetophenone still contained therein by extracting by boiling with five times 150 ml of diethyl ether. 2-Methyl-3-carbomethoxy-4-(2-nitrophenyl)-5-methylsulphonyl-6-phenyl-1,4-dihydropyridine, of melting point 264°–265° C, remains as the residue.

EXAMPLE 8

6.9 g of 3-aminocrotonic acid methyl ester and 13.9 g of phenylsulphonylacetone are added to 9.1 g of o-nitrobenz- aldehyde dissolved in 50 ml of hexamethylphosphoric acid triamide. The mixture is then stirred for 10 hours under nitrogen at a bath temperature of 110° C. The mixture is cooled and dissolved in 400 ml of ethyl acetate and the solution is washed with a mixture of 400 ml of water, 60 ml of methanol and 60 ml of saturated sodium chloride solution. The aqueous phase is separated off and the organic phase is washed with 3 times 100 ml of water, with twice 100 ml of 1 N hydrochloric acid solution, with twice 60 ml of saturated sodium bicarbonate solution and once with 60 ml of 2 N sodium carbonate solution. The ethyl acetate phase is dried over sodium sulphate and evaporated. The residue is chromatographed on silica gel using a mixture of toluene and ethyl acetate (7:3) as the eluant. The eluate is evaporated and crystallised from methanol. In this way, 2,6dimethyl-3-carbomethoxy-4-(2-nitrophenyl)-5- phenylsulphonyl-1,4-dihydropyridine, of melting point 203° C, is obtained.

2,6-Dimethyl-3-carbomethoxy-4-(2-nitrophenyl)-5-methylsulphinyl-1,4-dihydropyridine is obtained in a manner analogous to the preceding examples.

Example 9

Tablets containing 2,6-dimethyl-3-carbomethoxy-5-methylsulphonyl-4-(2-nitrophenyl)-1,4-dihydropyridine.

| Composition (for 10,000 tablets) | |
|---|---|
| 2,6-Dimethyl-3-carbomethoxy-5-methylsulphonyl-4-(2-nitrophenyl)-1,4-dihydropyridine | 500 g |
| Crystalline lactose | 60 g |
| Wheat starch | 20 g |
| Aerosil 200 | 87 g |
| Talc | 30 g |
| Magnesium stearate | 3 g |

Manufacture

The active substance is mixed with part of the wheat starch and with lactose and Aerosil 200 and the mixture is forced through a sieve. A further part of the wheat starch is made into a paste with the 5-fold amount of water on a water bath and the pulverulent mixture is kneaded with this paste until a slightly plastic mass has formed. The plastic mass is pressed through a sieve of about 3 mm mesh width and dried and the dry granules are again forced through a sieve. The remaining wheat starch, talc and magnesium stearate are then mixed in and the resulting mixture is pressed to give tablets with a cross-groove.

What we claim is:

1. A 1,4-dihydropyridine compound of the formula I

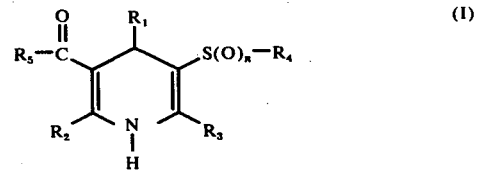

and their tautomers, wherein $R_1$ is unsubstituted phenyl or phenyl substituted by 1 or 2 identical or different substituents selected from the group consisting of nitro, trifluoromethyl, cyano, azido, lower alkanoyl, sulphamoyl, N-($C_{1-4}$) alkylsulphamoyl, N,N-di($C_{1-4}$)-alkylsulphamoyl, $R_2$ and $R_3$ independently of one another represent hydrogen, phenyl, phenyl-($C_{1-4}$)-alkyl or ($C_{1-7}$)-alkyl, $R_4$ represents ($C_{1-7}$)-alkyl or unsubstituted phenyl or phenyl substituted by ($C_{1-4}$)-alkyl, ($C_{1-4}$)-alkoxy, halogen or trifluoromethyl, $R_5$ represents (C1-4)-lower alkoxy, amino, mono- or di-($C_{1-4}$)-alkylamino, and $n$ is 1 or 2.

2. The 1,4-dihydropyridines as claimed in claim 1 of the formula I, wherein $R_1$ represents a phenyl radical which is substituted by 1 or 2 identical or different substituents from the group nitro, trifluoromethyl, cyano, azido, lower alkanoyl, sulphamoyl, N-($C_{1-4}$)-alkylsulphamoyl, N,N-di-($C_{1-4}$)-alkylsulphamoyl, at least one of the substituents being in the orthoposition, $R_2$ and $R_3$ independently of one another represent hydrogen, phenyl or ($C_{1-4}$)-alkyl, $R_4$ represents ($C_{1-7}$)-alkyl, phenyl, ($C_{1-4}$)-alkylphenyl, ($C_{1-4}$)-alkoxyphenyl, halogenophenyl or trifluoromethylphenyl, $R_5$ represents amino, mono- or di-($C_{1-4}$)-alkylamino or ($C_{1-4}$)-alkoxy, and $n$ is 1 or 2.

3. The 1,4-dihydropyridines as claimed in claim 1 of the formula I, wherein $R_1$ represents a phenyl radical which is substituted by 1 or 2 identical or different substituents from the group nitro, trifluoromethyl, cyano, azido, $(C_{1-4})$-lower alkanoyl, sulphamoyl, N-$(C_{1-4})$-alkylsulphamoyl and N,N-$(C_{1-4})$-dialkylsulphamoyl, at least one of the substituents being in the ortho-position, $R_2$ and $R_3$ independently of one another represent hydrogen or $(C_{1-4})$-alkyl, $R_4$ represents $(C_{1-4})$-alkyl or phenyl, $R_5$ represents amino, mono- or di-$(C_{1-4})$-alkylamino or $(C_{1-4})$-alkoxy and $n$ is 1 or 2.

4. The 1,4-dihydropyridines as claimed in claim 2 of the formula I, wherein $R_1$ represents a phenyl radical which is substituted by 1 or 2 identical or different substituents from the group nitro, trifluoromethyl, cyano, azido, $(C_{1-4})$-lower alkanoyl, sulphamoyl, N-$(C_{1-4})$-alkylsulphamoyl and N,N-$(C_{1-4})$-dialkylsulphamoyl, at least one of the substituents being in the ortho-position, $R_2$ and $R_3$ independently of one another represent hydrogen, $(C_{1-4})$-alkyl or phenyl, $R_4$ represents $(C_{1-4})$-alkyl or phenyl, $R_5$ represents amino- mono- or di-$(C_{1-4})$-alkylamino, or $(C_{1-4})$-alkoxy and $n$ is 1 or 2.

5. The 1,4-dihydropyridines of the claim 1, wherein $R_1$ denotes a phenyl radical which is substituted in the ortho position by nitro, trifluoromethyl, cyano, azido, $(C_{1-4})$-lower alkanoyl, sulphamoyl, N-$(C_{1-3})$-alkylsulphamoyl or N,N-di-$(C_{1-3})$-alkylsulphamoyl, $R_2$ and $R_3$ independently of one another represent hydrogen or $(C_{1-4})$-alkyl, $R_4$ represents $(C_{1-4})$-alkyl, $R_5$ represents amino, $(C_{1-4})$-lower alkylamino, $(C_{1-4})$-di-lower alkylamino or $(C_{1-4})$-alkoxy and $n$ is 1 or 2.

6. The 1,4-dihydropyridines as claimed in claim 2 of the formula I, wherein $R_1$ denotes a phenyl radical which is substituted in the ortho-position by cyano, azido, $(C_{1-4})$-lower alkanoyl, sulphamoyl, N-$(C_{1-3})$-alkylsulphamoyl, nitro, trifluoromethyl or N,N-di-$(C_{1-3})$-alkylsulphamoyl, $R_2$ and $R_3$ independently of one another represent hydrogen, $(C_{1-4})$-alkyl or phenyl, $R_4$ represents $(C_{1-4})$-alkyl or phenyl, $R_5$ represents amino, $(C_{1-4})$-lower alkylamino, di-$(C_{1-4})$-lower alkylamino, $(C_{1-4})$-alkoxy and $n$ is 1 or 2.

7. The 1,4-dihydropyridines as claimed in claim 2 of the formula I, wherein $R_1$ denotes a phenyl radical which is substituted in the ortho-position by nitro, trifluoromethyl or N,N-di-$(C_{1-3})$-alkylsulphamoyl, $R_2$ and $R_3$ independently of one another represent hydrogen, $(C_{1-4})$-alkyl or phenyl, $R_4$ represents $(C_{1-4})$-alkyl or phenyl, $R_5$ represents $(C_{1-4})$-alkoxy, and $n$ is 2.

8. The 1,4-dihydropyridines of the claim 1 wherein $R_1$ denotes a phenyl radical which is substituted in the orthoposition by nitro, trifluoromethyl, cyano, acetyl or sulphamoyl, $R_2$ and $R_3$ independently of one another denote hydrogen, methyl or ethyl, $R_4$ represents methyl or ethyl, $R_5$ represents amino, methylamino or dimethylamino or methoxy or ethoxy and $n$ is 1 or 2.

9. The 1,4-dihydropyridines as claimed in claim 2 of the formula I, wherein $R_1$ denotes a phenyl radical which is substituted in the ortho-position by cyano, acetyl, sulphamoyl, nitro, trifluoromethyl or N,N-di-$(C_{1-3})$-alkylsulphamoyl, $R_2$ and $R_3$ independently of one another denote hydrogen, methyl, ethyl or phenyl, $R_4$ represents methyl, ethyl or phenyl, $R_5$ represents amino, methylamino, dimethylamino, methoxy, ethoxy, and $n$ is 1 or 2.

10. The 1,4-dihydropyridines as claimed in claim 2 of the formula I, wherein $R_1$ denotes a phenyl radical which is substituted in the ortho-position by nitro, trifluoromethyl or N,N-di-(C1-3)-alkylsulphamoyl, $R_2$ and $R_3$ independently of one another denote hydrogen, methyl, ethyl or phenyl, $R_4$ represents methyl, ethyl or phenyl, $R_5$ represents methoxy, ethoxy, and $n$ is 2.

11. A compound selected from the group consisting of 2,6-Dimethyl-3-carbomethoxy-5-methylsulphonyl-4-(2-trifluoromethylphenyl)-1,4-dihydropyridine and 2,6-dimethyl-3-carbomethoxy-5-methylsulphonyl-4-(2-nitrophenyl)-1,4-dihydropyridine.

12. 2,6-Dimethyl-3-carbomethoxy-5-methylsulphonyl-4-(2-dimethylsulphamoyl-phenyl)-1,4-dihydropyridine.

13. A compound selected from the group consisting of 2,6-Dimethyl-3-(2-dimethylamino)-carboethoxy-4-(2-nitrophenyl-5-methylsulphonyl-1,4-dihydropyridine and 2,6-dimethyl-3-carbo-t.-butoxy-4-(2-nitrophenyl)-5-methylsulphonyl-1,4-dihydropyridine.

14. 2-Methyl-3-carbomethoxy-4-(2-nitrophenyl)-5-methyl-sulphonyl-6-phenyl-1,4-dihydropyridine or 2,6-dimethyl-3-carbomethoxy-4-(2-nitrophenyl)-5-phenylsulphonyl-1,4-dihydropyridine.

15. A pharmaceutical preparation useful for the treatment of hypertension which comprises an antihypertensively effective amount of a compound of claim 1 together with a therapeutically usable excipient.

* * * * *